United States Patent [19]

Donovan

[11] Patent Number: 4,845,923
[45] Date of Patent: Jul. 11, 1989

[54] CONTAMINATED SHARP OBJECT DISPOSAL METHOD

[76] Inventor: Dennis M. Donovan, 550 Thatcher Ave., River Forest, Ill. 60305

[21] Appl. No.: 82,440

[22] Filed: Aug. 6, 1987

[51] Int. Cl.⁴ .................. B65B 55/20; B65B 27/00
[52] U.S. Cl. .................................... 53/431; 53/440; 53/472; 53/474
[58] Field of Search .............. 53/431, 440, 472, 474, 53/140; 206/328

[56] References Cited

U.S. PATENT DOCUMENTS

| | | | |
|---|---|---|---|
| 624,972 | 5/1899 | Precht | 53/431 X |
| 1,842,456 | 1/1932 | MacKenzie | 53/472 X |
| 2,653,139 | 9/1953 | Sterling | 53/474 X |
| 2,836,942 | 6/1958 | Miskel | 53/440 X |
| 2,897,641 | 8/1959 | Simon et al. | 53/472 X |
| 3,585,275 | 6/1971 | Gillemot et al. | 206/328 X |
| 3,763,622 | 10/1973 | Stanley, Jr. | 53/474 X |
| 3,805,475 | 4/1974 | Glenn | 53/474 X |
| 3,830,895 | 8/1974 | Theodorsen | 53/474 X |
| 4,030,267 | 6/1977 | Arnaud | 53/474 X |
| 4,713,927 | 12/1987 | Rubens et al. | 53/472 |

FOREIGN PATENT DOCUMENTS 0023972  3/1978  Japan ...................................... 53/472

Primary Examiner—Horace M. Culver
Attorney, Agent, or Firm—Marshall, O'Toole, Gerstein, Murray & Bicknell

[57] ABSTRACT

A system and a method for the isolation from the environment of chemically or biologically contaminated objects are disclosed. The method includes inserting a contaminated object into a disposal container and then contacting the object with one or more reactive agents which react to immobilize and protectively encapsulate the object. The use of reactive agents which are members of room temperature reacting polyurethane foam systems is particularly preferred.

17 Claims, 2 Drawing Sheets

CONTAMINATED SHARP OBJECT DISPOSAL METHOD

BACKGROUND OF THE INVENTION

The present invention relates generally to methods for the isolation and disposal of chemically and biologically contaminated objects. More specifically, the invention relates to methods and systems whereby objects with sharp points and/or edges such as hypodermic needles and scalpels are protectively isolated until they can be safely disposed of.

Chemically and biologically contaminated materials represent a potential health hazard to all persons who come into contact with them. This health hazard can be extreme in the case of powerful toxins and deadly infective agents such as the hepatitis virus or the human immunodeficiency virus (HIV) responsible for acquired immune deficiency syndrome (AIDS). Materials which present particularly high risks of exposure are those which have sharp edges or points and which are therefore easily capable of puncturing protective clothing and breaking the skin. Particularly dangerous objects include hypodermic needles, scalpel blades, suture needles and catheters as well as materials such as micropipette tubes and other glassware which can have sharp points and edges and are capable of rupturing the skin.

Individuals at risk from such contaminated sharp objects include not only those who directly administer patient care or work in laboratories, but also those hospital housekeeping employees involved in the internal disposal process. Increased training of all personnel will reduce hazards, but even the most highly trained health care workers, including nurses and physicians, sustain inadvertent needle sticks and other wounds. Significantly, many needle sticks occur in the process of recapping used needles. Essential though it is, training is not the entire solution.

Since generally only incineration can provide adequate assurance of a contaminant's destruction, there is likely to be a delay between the use of an object and its eventual destruction. During this period, contaminated products are handled by workers outside the health care establishment, including refuse workers, waste haulers and incinerator workers, who may or may not be adequately trained or supervised. The risks posed to these workers present a significant need for improved methods for the isolation and disposal of chemically and biologically contaminated objects.

SUMMARY OF THE INVENTION

According to the invention, a method for the isolation from the environment of chemically or biologically contaminated objects is provided wherein the objects are inserted into a disposal container and are contacted with one or more agents which react to form a reaction product which immobilizes and protectively encapsulates the object.

In addition to the isolation method, the invention comprehends a system for the isolation from the environment of chemically or biologically contaminated objects including a disposal container, one or more reactive agents capable of being reacted to protectively encapsulate said objects when the objects are placed in the container, and means for activating the reactive agents.

Other advantages will be apparent to those skilled in the art from the following detailed description taken in conjunction with the drawings and appended claims.

DETAILED DESCRIPTION OF THE INVENTION

Figure 1A:
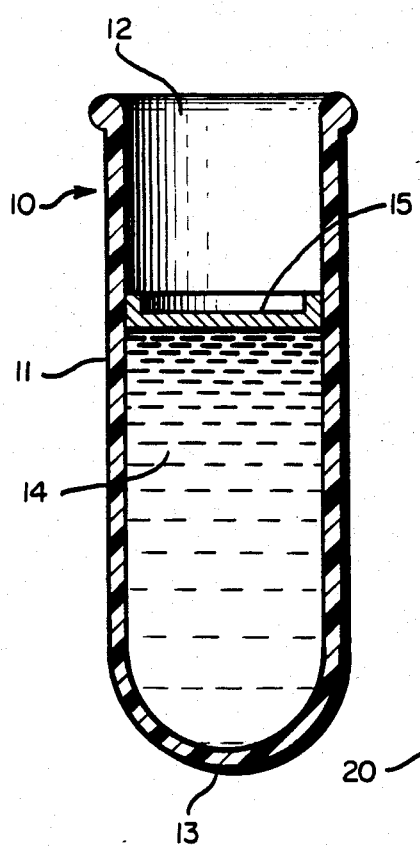
FIG. 1a is a depiction of a device according to the present invention wherein a mixture of reactive agents is incorporated into the disposal container of the device.

According to the invention, a method and a system for the isolation from the environment of chemically and biologically contaminated objects and particularly those objects having sharp points or edges (contaminated "sharps") are provided. The method constitutes an improved means of disposal for contaminated objects whereby the objects may be isolated from the environment at the point of use in such a way that the likelihood of inadvertent injury is significantly reduced or substantially eliminated. The method does not necssarily destroy or inactivate chemical or biological contaminants, but rather promotes increased safety by providing an improved and multiple barrier between the contaminated object and the environment. The method immobilizes and encapsulates the contaminated object in a disposal container and thus isolates the object from the environment and protects workers until it can be permanently disposed of, whether by incineration, compaction and isolation, or other means.

The method involves immobilization and encapsulation of the contaminated sharp by reactive material such as a polymer or polymer foam in a disposal container. The disposal container, which may be fabricated in a variety of shapes and sizes according to the size and number of objects to be disposed of therein, is preferably a tube manufactured from a combustible plastic or a low-melting metal such as aluminum. The disposal container may be relatively small, that is, test tube size, where it is intended to isolate one or a small number of objects such as hypodermic needles or scalpel blades. Alternatively, much larger containers can be utilized as containment stations in health care facilities. Reactive agents may be periodically applied to such containment stations so as to immobilize and encapsulate "layers" of contaminated material. The use of plastic disposal containers is preferred because their combustibility makes them particularly suitable for incineration. The disposal containers may be appropriately marked as to the nature of the hazard involved. The reactive agents and means for their activation, as well as the shape and texture of the disposal containers, are selected such that the contaminated materials cannot readily be freed from encapsulation by normal handling. According to some applications, the encapsulating material is preferably a polymer foam or similar material.

According to one embodiment of the invention, the isolation system comprises a container, such as a test tube, containing two reactive agents capable, when mixed, of reacting to form a porous or nonporous (e.g., closed cell) plastic foam or a plastic solid. The reactive agents may be isolated in said disposal container by means such as membranes or encapsulation such that the reaction system is activated by rupturing said encapsulation or membranes and mixing the reactive agents. The membranes may be ruptured and agents mixed and activated by means of the contaminated object itself.

According to an alternative embodiment, at least one of the reactive agents is not originally present in the disposal container, but is introduced into the container from an external source such as a pressurized device which may be activated by a valve.

According to another alternative embodiment, reactive agents may be maintained in the presence of one another whereby at least one such reactive agent may be activated by physical or chemical means including activation by heat or electromagnetic energy.

Referring to FIG. 1a, a device, generally designated 10 for the isolation from the environment of chemically or biologically contaminated objects is shown. The device 10 comprises a disposal container 11 open at one end 12 and closed at the opposite end 13 containing, for example, a mixture of reactive agents 14 which may include a heat activatable blocked isocyanate reactive agent. The mixture of reactive agents 14 is retained by a membrane 15 which may be fashioned from a material such as metal foil or plastic which is impervious to the reactive agents but which may readily be ruptured by an inserted contaminated object. According to a method of utilizing the device 10, a contaminated sharp such as a hypodermic needle on a syringe is inserted into the interior of the container 11 through the open end 12 piercing the membrane 15 and the mixture of reactive agents. After one or more contaminated objects have been inserted into the disposal container 11, the reactive agents may be activated, such as by heating in a microwave oven.

Figure 1B:
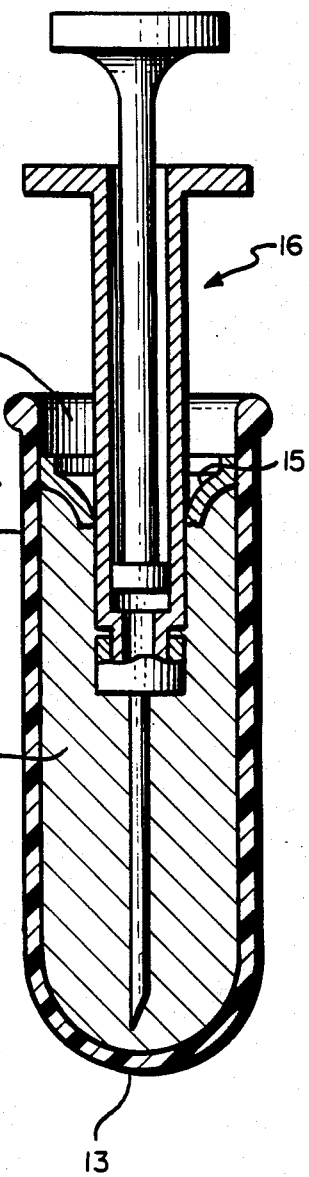
FIG. 1b is a depiction of the device of FIG. 1a used to immobilize and encapsulate a contaminated object.

Referring to FIG. 1b, the device 10 is shown wherein a contaminated syringe 16 has been inserted into the disposal container 11 and wherein the reactive agents 14 have been activated to react and immobilize and encapsulate the syringe 16. The reactive agents may be selected to form a glassy solid or may preferably be selected to produce a solid foam which expands to fill the volume of the disposal container, thus encapsulating not just the sharp point or edge, but any desired portion of the contaminated object.

Depending on the identity and nature of the specific reactive agents selected, a high degree of mixing of the reactive agents may be desired to achieve the best results. For this reason, various means may be utilized to provide for complete mixing and activation of the reactive agents. Suitable means include plungers or stirrers incorporated with the devices of the invention. Also, stirring may be accomplished using the contaminated object itself. Such mixing means may also be utilized to rupture membranes or other means separating the reactive agents. According to various embodiments, the reactive agents may be encapsulated with various inert materials whereby the agents are activated upon rupturing of the encapsulation by physical or chemical means including the use of heat or electromagnetic radiation.

Figure 2:
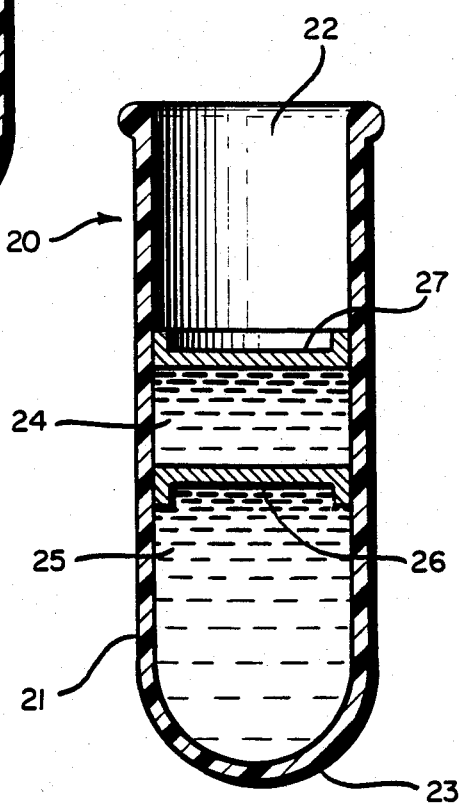
FIG. 2 is a depiction of a device according to the present invention including a liquid reactive agent and a porous reactive agent.

Referring to FIG. 2, an alternative device generally designated 20 for the isolation from the environment of contaminated objects is shown. The device 20 comprises a disposal container 21, open at an end 22 and closed at the opposite end 23, including a liquid first reactive agent 24 and a porous foam 25 comprising or impregnated with a second reactive agent. A first membrane 26 separates the porous foam 25 from the first reactive agent 24 while a second membrane 27 is used to retain the first reactive agent in the disposal container 21. According to a method of utilizing the device 20, a contaminated sharp such as a hypodermic needle on a syringe is inserted into the interior of the container 21 through the open end 22, thus piercing the second membrane 27, the first reactive agent 24, the first membrane 26 and the impregnated foam 25. The first reactive agent 24 is then absorbed by the foam as a consequence of capillary action and/or gravity with the result that the first and second reactive agents react to harden the porous foam and encapsulate and fix the contaminated object in place.

According to an alternative embodiment of the invention, at least one of the reactive agents is not initially placed in the disposal container, but is instead introduced into said disposal container by means of a pressurized device. Such devices can include aerosol containers, metallic cylinders containing pressurized gas or gas mixtures, and pumps or compressors. The reactive agent, when introduced into the disposal container, reacts to encapsulate and immobilize the contaminated object. Where two or more reactive agents are maintained under pressure, they may be introduced into the disposal container by means of a mixing valve which intimately mixes the reactive agents, activating them and causing them to react. Disposal systems may be provided whereby single object disposal containers may be placed onto a device including pressurized reactive agents, tubing, valves, and alignment means for positioning the disposal container whereby insertion of the contaminated object activates a valve, prompting the admission of the reactive agents into the disposal container, thus encapsulating and immobilizing the contaminated object. The disposal container containing the contaminated object, thus encapsulated and immobilized, may be removed from the device and subjected to interim containment until final disposal. Meanwhile, the device may be reused with other disposal containers.

Where the system of the invention is used as a containment station for disposal of a large number of contaminated objects, means for application and activation of the reactive agents may be provided whereby "layers" of contaminated material may be immobilized and encapsulated. The use of one and two component polyurethane "foam-in-place" systems are particularly suitable for such applications.

Figure 3A:
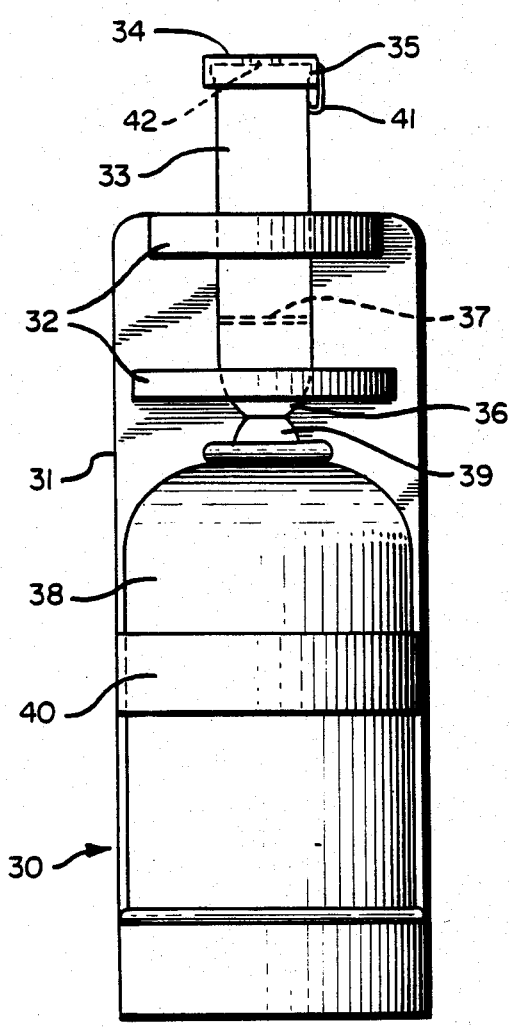
FIG. 3 depicts a system according to the invention including a pressurized device for storage of a reactive agent.
Figure 3B:
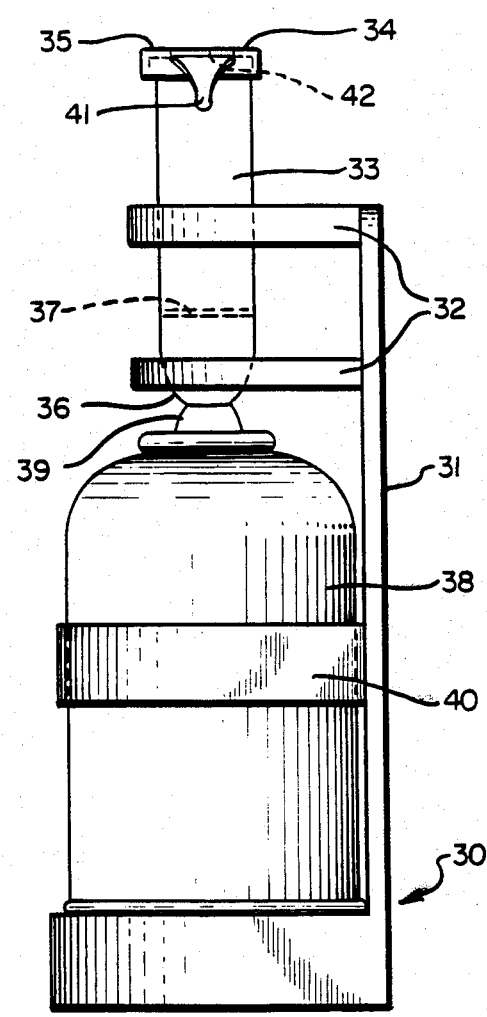
Figure 4A:
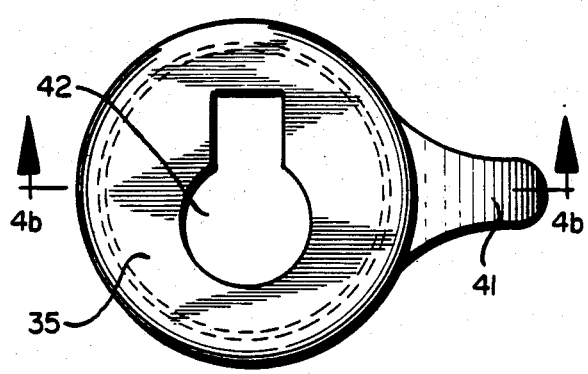
FIGS. 4a and 4b depict a disposal tube cap useful with devices according to the present invention.
Figure 4B:
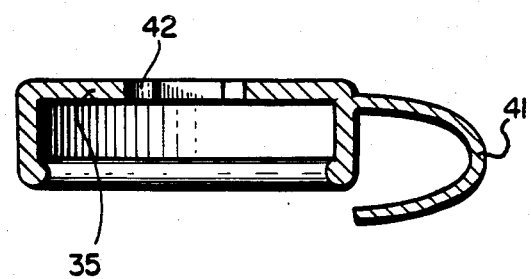

Referring to FIGS. 3a and 3b, a system generally designated 30 for the isolation from the environment of contaminated objects is shown. The system comprises a holding device 31 which provides mechanical support for the components of the system. Alignment rings 32 provide for alignment of a disposal tube 33 having a first end 34 partially covered by a disposal tube cap 35 defining an opening 42 and a second end 36 which is open but which is optionally occluded by a baffle 37 which is permeable to the reactive agents of the invention but which prevents a contaminated object inserted at the first end 34 from protruding through the second end 36. The disposal tube cap 35 may optionally be attached to the disposal tube 33 by means of a tether 41. The cap 35 defines a stepped keyhole opening 42 for the removal of detachable needles. The system also includes a pressurized container 38 supplying one or more reactive agents through a valve 39 into the opening on the second end 36 of the disposal tube 33. The pressurized container is held in place by means of a restraining strap 40.

According to a method of utilizing the system 30, a contaminated sharp object such as a hypodermic needle on a syringe is inserted into the interior of the disposal tube 33 through the opening 42 in the disposal tube cap 35 on the first end 34 of the disposal tube. The disposal tube 33 is pressed down, thus activating the valve 39 on the pressurized container 38. One or more reactive agents are admitted through the second end 36 of the disposal tube passing through the baffle 37, where provided, and filling the disposal tube 33. In the course of filling the disposal tube 33, the reactive agents will tend to float the contaminated object away from the second end 36, to some degree obviating the need for a baffle 37. The reactive agents then react to form a porous or glassy solid thus immobilizing and encapsulating the contaminated sharp in the disposal tube 33. The disposal tube 33 containing the immobilized and encapsulated contaminated object may then be removed from the alignment rings 32 and subjected to interim disposal while a fresh disposal tube 33 may be inserted into the alignment rings 32 in order that the process may be repeated.

At the conclusion of the encapsulation and immobilization process, the disposal container of the invention may be removed from its holder and subjected to interim containment until final disposal. Various methods are available for interim containment including bagging in appropriately marked plastic bags or other sharps receptors at or near the point of use. The devices may also be placed into the hopper of a waste compactor which would reduce the volume of the waste. For greatest safety, the compaction would take place within a metallic or polymeric cylinder which could then be sealed with a metal or polymeric cap. Final disposal could be by burial or incineration depending upon the nature of the contamination. Nevertheless, incineration according to known techniques within the art is generally preferred with the materials of the disposal devices being selected so as to be particularly suitable for incineration. Where disposal is to be by incineration, polymeric cylinder and cap materials are particularly preferred because of their combustibility.

Reactive agents useful according to the present invention include those agents which are capable of reacting to form a stable solid material. Preferred agents are those which are capable of activation and reaction at room temperature. Components of polymer systems are generally useful as the reactive agents of the invention, it being well within the skill of the art to select combinations of resins, crosslinking agents, catalysts, promoters, foaming agents and the like to produce reaction systems capable of rapid polymerization at room temperature.

Particularly preferred is the use of reactive agents which are components of polymer foam systems. Such agents are particularly useful as a consequence of their ability to expand upon reaction and consume a greater volume of space than they would in an unreacted state. This characteristic is useful for devices wherein the reactive agents are encapsulated and stored within the disposal container as well as with devices and systems wherein one or more of the reactive agents is stored in a pressurized device. Moreover, the use of reactive agents which expand upon reaction tends to more fully and better encapsulate and immobilize the contaminated objects. Polymer foam systems can be readily combustible which represents a distinct advantage where final disposal is to be by incineration.

A class of reactive agents which is particularly useful according to the invention includes those agents which are members of polyurethane foam reaction systems. Polyurethanes are produced by reaction of an isocyanate with reactive polyolefin resin materials such as polyols generally characterized by molecular weights in excess of 1000. Various other materials such as low molecular weight chain extenders, catalysts, promoters and foaming agents are also typically included in polyurethane reaction systems. The identity and proportions of the reactive agents may be selected by those of skill in the art to polymerize under a variety of conditions to produce products with wide varieties of properties.

Multi-component reaction systems may be selected such that reaction is initiated upon mixing of two or more of the reactive agents. Heat activated reaction systems may also be selected wherein application of heat energy, either directly, or by means of microwave or other electromagnetic radiation activates a polymerization reaction. Reactive agents suitable for use with the invention include "blocked" isocyanates, which are known for use in a variety of polyurethane reaction systems, including coating systems and adhesive systems. At elevated temperatures, the blocked isocyanate agents are activated and behave as free isocyanates capable of reaction with reactive polyolefins.

A preferred means of practicing the invention involves the use of what are known to the art as "foam-in-place" polyurethane formulations. Such formulations typically include a reactive polyolefin such as a reactive polyol and a polymeric isocyanate along with a catalyst and a blowing agent and are used for applications such as the on-site formation of building insulation. Two component systems are known wherein reactive agents from two pressurized containers are mixed in a mixing valve and allowed to produce a foam in a closed space. Typical of such systems is the FrothPak ® two component system (Insta-Foam Products, Inc., Joliet, Ill.) including as component A a polymeric isocyanate and as component B a polyether polyolefin including additives such as a catalyst and a blowing agent. Components A and B are mixed in selected proportions at room temperature and the reactive agents react to produce a solid polyurethane foam. One-component foam-in-place products are also known wherein all components and reactive agents are premixed and maintained under pressure in a pressurized container. These systems are activated and produce a rigid foam upon release to the atmosphere. Suitable one-component foam-in-place products include those such as Insta-Seal ® and Great Stuff ® room temperature curing systems available from Insta-Foam Products, Inc. Similar systems and reactive agents are available from a wide variety of sources and are readily designed to exhibit various reaction characteristics and final properties.

The foregoing detailed description is given for clearness of understanding only, and no unnecessary limitations are to be understood therefrom, as modifications within the scope of the invention will be obvious to those skilled in the art.

What is claimed is:

1. A method for the isolation from the environment of a chemically or biologically contaminated object having at least one sharp point or edge, said method comprising the steps of:

(a) inserting said object into a disposal container, (b) contacting said object with at least one reactive agent, and (c) reacting said agent in response to said inserting step to immobilize and protectively encapsulate said object.

2. The method according to claim 1 wherein said object is selected from the group consisting of hypodermic needles, scalpels, suture needles, catheters and glassware.

3. The method according to claim 1 wherein said object is contacted with more than one reactive agent and wherein at least one of said reactive agents is isolated in said disposal container by a rupturable containment means and wherein said containment means is ruptured and the reactive agents are thereby mixed and react upon insertion of said object into said disposal container.

4. The method according to claim 1 wherein said at least one reactive agent is activated to react upon application of heat or electromagnetic energy.

5. The method according to claim 4 wherein one of said reactive agents is a blocked isocyanate.

6. The method according to claim 1 wherein at least one of said reactive agents is introduced into said disposal container by means of a pressurized device.

7. The method according to claim 6 wherein two or more of said reactive agents are mixed by means of a mixing valve.

8. The method according to claim 1 wherein said reactive agents are members of a polymer reaction system.

9. The method according to claim 8 wherein said reaction system is a polyurethane foam system.

10. The method according to claim 1 wherein said reaction system is capable of reacting at room temperature.

11. A method for the isolation from the environment of a chemically or biologically contaminated object, said method comprising the steps of:

(a) inserting said object into a disposal container, (b) contacting said object with more than one reactive agents, and (c) reacting said agents to immobilize and protectively encapsulate said object wherein at least one of said reactive agents is isolated in said disposal container by a rupturable containment means and wherein said containment means is ruptured and the reactive agents are thereby mixed and react upon insertion of said object into said disposal container.

12. The method according to claim 11 wherein said object has at least one sharp point or edge and is selected from the group consisting of hypodermic needles, scalpels, suture needles, catheters and glassware.

13. The method according to claim 11 wherein at least one of said reactive agents is activated to react upon application of heat or electromagnetic energy.

14. The method according to claim 13 wherein one of said reactive agents is a blocked isocyanate.

15. The method according to claim 11 wherein said reactive agents are members of a polymer reaction system.

16. The method according to claim 15 wherein said reaction system is a polyurethane foam system.

17. The method according to claim 11 wherein said reaction system is capable of reacting at room temperature.

* * * * *